(12) United States Patent
Mahajan et al.

(10) Patent No.: US 10,617,320 B2
(45) Date of Patent: *Apr. 14, 2020

(54) METHOD TO TRIGGER AN ATRIAL FIBRILLATION ELECTROGRAM IN AN IMPLANTABLE DEVICE THAT DETECTS R-WAVES

(71) Applicant: Cardiac Pacemakers, Inc., St. Paul, MN (US)

(72) Inventors: Deepa Mahajan, Roseville, MN (US); David L. Perschbacher, Coon Rapids, MN (US); Keith L. Herrmann, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 122 days.

This patent is subject to a terminal disclaimer.

(21) Appl. No.: 15/175,151

(22) Filed: Jun. 7, 2016

(65) Prior Publication Data

US 2017/0027462 A1    Feb. 2, 2017

Related U.S. Application Data

(60) Provisional application No. 62/199,022, filed on Jul. 30, 2015.

(51) Int. Cl.
*A61B 5/046* (2006.01)
*A61N 1/362* (2006.01)
(Continued)

(52) U.S. Cl.
CPC ............ *A61B 5/046* (2013.01); *A61B 5/0432* (2013.01); *A61B 5/686* (2013.01); *A61N 1/3624* (2013.01);
(Continued)

(58) Field of Classification Search
CPC ....... A61N 1/395; A61N 1/3624; A61B 5/046
See application file for complete search history.

(56) References Cited

U.S. PATENT DOCUMENTS 5,562,709 A * 10/1996 White .................. A61N 1/3621
600/518
5,622,178 A    4/1997 Gilham
(Continued)

FOREIGN PATENT DOCUMENTS

CN    106659407 A    5/2017
CN    107529988 A    1/2018
(Continued)

OTHER PUBLICATIONS

"U.S. Appl. No. 14/825,669, Response filed Apr. 24, 2017 to Final Office Action dated Mar. 9, 2017", 12 pgs.
(Continued)

*Primary Examiner* — George R Evanisko
(74) *Attorney, Agent, or Firm* — Schwegman Lundberg & Woessner, P.A.

(57) ABSTRACT

An apparatus includes a sensing circuit configured to generate a sensed physiological signal representative of cardiac activity of a subject, an arrhythmia detection circuit, a control circuit, and a memory. The arrhythmia detection circuit detects an episode of atrial fibrillation (AF) in the sensed cardiac signal using a first AF detection criterion, and detects the episode of AF using a second AF detection criterion. The first AF detection criterion has greater sensitivity to AF detection than the second AF detection criterion, and the second AF detection criterion has greater specificity to AF detection than the first AF detection criterion. The control circuit initiates storing of sampled values of a segment of the cardiac signal that includes the episode of AF
(Continued)

when the episode of AF is detected by both the first AF detection criterion and the second AF detection criterion.

20 Claims, 9 Drawing Sheets

(51) Int. Cl.

| | | |
|---|---|---|
| *A61N 1/39* | (2006.01) | |
| *A61B 5/0432* | (2006.01) | |
| *A61B 5/00* | (2006.01) | |
| *A61N 1/365* | (2006.01) | |
| *A61B 5/0464* | (2006.01) | |
| *A61B 5/0205* | (2006.01) | |
| *A61B 5/0215* | (2006.01) | |
| *A61B 5/0245* | (2006.01) | |
| *A61B 5/0404* | (2006.01) | |
| *A61B 7/02* | (2006.01) | |

(52) U.S. Cl.
CPC ......... *A61N 1/36514* (2013.01); *A61N 1/395* (2013.01); *A61N 1/3956* (2013.01); *A61N 1/3987* (2013.01); *A61B 5/0205* (2013.01); *A61B 5/0215* (2013.01); *A61B 5/0245* (2013.01); *A61B 5/0404* (2013.01); *A61B 5/0464* (2013.01); *A61B 5/7221* (2013.01); *A61B 7/023* (2013.01)

(56) References Cited

U.S. PATENT DOCUMENTS

| | | | |
|---|---|---|---|
| 6,490,479 | B2 | 12/2002 | Bock |
| 6,931,273 | B2 | 8/2005 | Groenewegen et al. |
| 7,031,765 | B2 | 4/2006 | Ritscher et al. |
| 7,115,096 | B2 | 10/2006 | Siejko et al. |
| 7,353,057 | B2 | 4/2008 | Schiessle et al. |
| 7,412,282 | B2 | 8/2008 | Houben |
| 7,566,308 | B2 | 7/2009 | Stahmann |
| 7,596,405 | B2 | 9/2009 | Kurzweil et al. |
| 7,634,310 | B2 | 12/2009 | Lee et al. |
| 7,657,307 | B2 | 2/2010 | Van Dam et al. |
| 7,899,531 | B1 | 3/2011 | Benser et al. |
| 7,904,142 | B2 | 3/2011 | Kim et al. |
| 7,970,468 | B1* | 6/2011 | Ostrow ............ A61N 1/37247 600/518 |
| 8,195,280 | B2 | 6/2012 | Van Dam et al. |
| 8,326,407 | B2 | 12/2012 | Linker |
| 8,560,058 | B2 | 10/2013 | Babaeizadeh et al. |
| 8,639,316 | B2 | 1/2014 | Sarkar |
| 9,999,368 | B2 | 6/2018 | Perschbacher et al. |
| 2001/0034539 | A1 | 10/2001 | Stadler et al. |
| 2002/0065473 | A1 | 5/2002 | Wang et al. |
| 2004/0092836 | A1 | 5/2004 | Ritscher et al. |
| 2005/0080347 | A1 | 4/2005 | Sheth et al. |
| 2006/0247548 | A1 | 11/2006 | Sarkar et al. |
| 2007/0038253 | A1 | 2/2007 | Kim et al. |
| 2007/0100248 | A1 | 5/2007 | Van Dam et al. |
| 2008/0161703 | A1 | 7/2008 | Houben et al. |
| 2008/0288009 | A1 | 11/2008 | Kim et al. |
| 2009/0112110 | A1 | 4/2009 | Zhang |
| 2010/0057152 | A1 | 3/2010 | Kim et al. |
| 2010/0168597 | A1 | 7/2010 | Kim et al. |
| 2010/0274149 | A1 | 10/2010 | Li et al. |
| 2010/0305642 | A1 | 12/2010 | Dong et al. |
| 2011/0152957 | A1 | 6/2011 | Shaquer |
| 2012/0035489 | A1 | 2/2012 | Dong et al. |
| 2012/0101541 | A1 | 4/2012 | Corbucci et al. |
| 2012/0238891 | A1 | 9/2012 | Sarkar et al. |
| 2012/0238892 | A1 | 9/2012 | Sarkar |
| 2013/0150911 | A1 | 6/2013 | Perschbacher et al. |
| 2013/0296680 | A1* | 11/2013 | Linker ............... A61B 5/04012 600/391 |
| 2015/0088216 | A1 | 3/2015 | Gordon et al. |
| 2016/0045125 | A1 | 2/2016 | Krueger et al. |
| 2016/0287115 | A1 | 10/2016 | Perschbacher et al. |
| 2017/0127965 | A1 | 5/2017 | Krueger et al. |
| 2018/0256053 | A1 | 9/2018 | Perschbacher et al. |

FOREIGN PATENT DOCUMENTS

| | | |
|---|---|---|
| CN | 107847746 A | 3/2018 |
| EP | 2407097 A1 | 1/2012 |
| EP | 3259027 A1 | 12/2017 |
| EP | 3277372 A1 | 2/2018 |
| JP | H10127590 A | 5/1998 |
| JP | H11503038 A | 3/1999 |
| JP | 2008539015 A | 11/2008 |
| JP | 2012527958 A | 11/2012 |
| JP | 2017527356 A | 9/2017 |
| JP | 2018523518 A | 8/2018 |
| WO | WO-2006118852 A2 | 11/2006 |
| WO | WO-2013020710 A1 | 2/2013 |
| WO | WO-2016025704 A1 | 2/2016 |
| WO | WO-2016134161 A1 | 8/2016 |
| WO | WO-2016160674 A1 | 10/2016 |
| WO | WO-2017019178 A1 | 2/2017 |
| WO | WO-2017079245 A1 | 5/2017 |

OTHER PUBLICATIONS

"U.S. Appl. No. 14/825,669, Advisory Action dated May 3, 2017", 3 pgs.

"U.S. Appl. No. 14/825,669, Appeal Brief filed Dec. 26, 2017", 17 pgs.

"U.S. Appl. No. 14/825,669, Final Office Action dated Mar. 9, 2017", 13 pgs.

"U.S. Appl. No. 14/825,669, Non Final Office Action dated Jun. 23, 2017", 9 pgs.

"U.S. Appl. No. 14/825,669, Non Final Office Action dated Sep. 27, 2016", 9 pgs.

"U.S. Appl. No. 14/825,669, Response filed Jun. 8, 2017 to Final Office Action dated Mar. 9, 2017", 14 pgs.

"U.S. Appl. No. 15/082,440, Corrected Notice of Allowance dated Feb. 9, 2018", 5 pgs.

"U.S. Appl. No. 15/082,440, Examiner Interview Summary dated Sep. 6, 2017", 2 pgs.

"U.S. Appl. No. 15/082,440, Non Final Office Action dated Jun. 21, 2017", 9 pgs.

"U.S. Appl. No. 15/082,440, Notice of Allowance dated Jan. 18, 2018", 8 pgs.

"U.S. Appl. No. 15/082,440, Notice of Allowance dated Sep. 25, 2017", 10 pgs.

"U.S. Appl. No. 15/082,440, Response filed May 17, 2017 to Restriction Requirement dated Mar. 30, 2017", 9 pgs.

"U.S. Appl. No. 15/082,440, Response filed Sep. 5, 2017 to Non Final Office Action dated Jun. 21, 2017", 14 pgs.

"U.S. Appl. No. 15/082,440, Restriction Requirement dated Mar. 30, 2017", 7 pgs.

"Application Serial No. PCT/US2016/036146, Invitation to Pay Add'l Fees and Partial Search Report dated Oct. 6, 2016", 7 pgs.

"Australian Application Serial No. 2015301633, First Examiners Report dated Sep. 7, 2017", 3 pgs.

"Australian Application Serial No. 2015301633, Response filed Mar. 21, 2018 to First Examiners Report dated Sep. 7, 2017", 14 pgs.

"European Application Serial No. 15757059.9, Response filed Sep. 26, 2017 to Communication Pursuant to Rules 161(1) and 162 EPC dated Mar. 21, 2017", 18 pgs.

"International Application Serial No. PCT/US2015/045042, International Preliminary Report on Patentability dated Feb. 23, 2017", 10 pgs.

"International Application Serial No. PCT/US2015/045042, International Search Report dated Oct. 27, 2015", 6 pgs.

"International Application Serial No. PCT/US2015/045042, Written Opinion dated Oct. 27, 2015", 9 pgs.

(56) References Cited

OTHER PUBLICATIONS

"International Application Serial No. PCT/US2016/024463, International Preliminary Report on Patentability dated Oct. 12, 2017", 8 pgs.
"International Application Serial No. PCT/US2016/024463, International Search Report dated Jun. 17, 2016", 6 pgs.
"International Application Serial No. PCT/US2016/024463, Written Opinion dated Jun. 17, 2016", 6 pgs.
"International Application Serial No. PCT/US2016/036146, International Preliminary Report on Patentability dated Feb. 8, 2018", 12 pgs.
"International Application Serial No. PCT/US2016/036146, International Search Report dated Dec. 7, 2016", 5 pgs.
"International Application Serial No. PCT/US2016/036146, Written Opinion dated Dec. 7, 2016", 10 pgs.
"International Application Serial No. PCT/US2016/060050, International Search Report dated Feb. 6, 2017", 4 pgs.
"International Application Serial No. PCT/US2016/060050, Written Opinion dated Feb. 6, 2017", 5 pgs.
"Japanese Application Serial No. 2017-508064, Office Action dated Mar. 6, 2018", (English Translation), 4 pgs.
Babaeizadeh, Saeed, et al., "Improvements in atrial fibrillation detection for real-time monitoring", Journal of Electrocardiology, Elsevier Science vol. 42, No. 6,, (Nov. 1, 2009), 522-526.
Esperer, et al., "Cardiac arrhythmias imprint specific signatures on Lorenz plots", Ann Noninvasive Electrocardiol, (2008), 44-60 pgs.
Pürerfellner, H., et al., "P-wave evidence as a method for improving algorithm to detect atrial fibrillation in insertable cardiac monitors", Heart Rhythm; vol. 11, Issue 9, (Sep. 2014), 1575-1583.
Tateno, K, et al., "Automatic detection of atrial fibrillation using the coefficient of variation and density histograms of RR and RR intervals", Medical and Biological Engineering and Computing, vol. 39, No. 6,, (Nov. 1, 2011), 664-671.
"European Application Serial No. 16730174.6, Response filed Sep. 25, 2018 to Communication Pursuant to Rules 161 and 162 EPC dated Mar. 23, 2018", 29 pgs.
"European Application Serial No. 16730174.6, Communication Pursuant to Article 94(3) EPC Dec. 18, 2018", 6 pgs.
"Japanese Application Serial No. 2018-504913, Notification of Reasons for Rejection dated Nov. 13, 2018", W/English Translation, 12 pgs.

\* cited by examiner

US 10,617,320 B2

METHOD TO TRIGGER AN ATRIAL FIBRILLATION ELECTROGRAM IN AN IMPLANTABLE DEVICE THAT DETECTS R-WAVES

CLAIM OF PRIORITY

This application claims the benefit of priority under 35 U.S.C. § 119(e) of U.S. Provisional Patent Application Ser. No. 62/199,022, filed on Jul. 30, 2015, which is herein incorporated by reference in its entirety.

BACKGROUND

Ambulatory medical devices include implantable medical devices (IMDs), wearable medical devices, handheld medical devices, and other medical devices. Some examples of IMDs include cardiac function management (CFM) devices such as implantable pacemakers, implantable cardioverter defibrillators (ICDs), subcutaneous implantable cardioverter defibrillators (S-ICDs), cardiac resynchronization therapy devices (CRTs), and devices that include a combination of such capabilities. The devices can be used to treat patients or subjects using electrical or other therapy, or to aid a physician or caregiver in patient diagnosis through internal monitoring of a patient's condition.

Some implantable medical devices can be diagnostic-only devices, such as implantable loop recorders (ILRs) and subcutaneously implantable heart failure monitors (SubQ HFMs). The devices may include electrodes in communication with one or more sense amplifiers to monitor electrical heart activity within a patient, or can include one or more sensors to monitor one or more other internal patient parameters. Subcutaneously implantable devices may include electrodes that are able to sense cardiac signals without being in direct contact with the patient's heart. Other examples of IMDs include implantable drug delivery systems or implantable devices with neural stimulation capability (e.g., vagus nerve stimulator, baroreflex stimulator, carotid sinus stimulator, spinal cord stimulator, deep brain stimulator, etc.).

Some examples of wearable medical devices include wearable cardioverter defibrillators (WCDs) and wearable diagnostic devices (e.g., an ambulatory monitoring vest, holter monitor, cardiac event monitor, or mobile cardiac telemetry devices). WCDs can be monitoring devices that include surface electrodes. The surface electrodes may be arranged to provide one or both of monitoring to provide surface electrocardiograms (ECGs) and delivery of cardioverter and defibrillator shock therapy. In some examples, a wearable medical device can also include a monitoring patch worn by the patient such as an adherable patch or can be included with an article of clothing worn by the patient.

Some examples of handheld medical devices include personal data assistants (PDAs) and smartphones. The handheld devices can be diagnostic devices that record an electrocardiograph (ECG) or other physiological parameter while the device is resting in the patient's hand or being held to the patient's chest.

CFM devices can be implantable but in some situations may not include dedicated atrial sensing capability. Additionally, some diagnostic-only implantable, wearable, and handheld devices do not include dedicated atrial sensing capability. Patients with these types of devices may develop atrial arrhythmias, such as atrial fibrillation (AF) for example. This is especially true for heart failure patients who typically have a high incidence of AF. Knowledge that a specific patient is experiencing AF can be useful to physicians and clinicians for diagnostic purposes or to tailor performance of a medical device to that patient's needs to provide the most effective patient therapy.

OVERVIEW

It can be desirable for ambulatory medical devices to correctly detect and identify cardiac arrhythmias. This can help to provide the most effective device-based therapy or non-device based therapy for the patient. The present subject matter relates to improving detection of atrial fibrillation and recording the fibrillation episode.

One example apparatus of the present subject matter can include a sensing circuit, an arrhythmia detection circuit, a memory, and a control circuit. The sensing circuit is configured to generate a sensed cardiac signal representative of cardiac activity of a subject. The arrhythmia detection circuit is configured to detect an episode of atrial fibrillation (AF) in the sensed cardiac signal using a first AF detection criterion, and detect the episode of AF using a second AF detection criterion. The first AF detection criterion has greater sensitivity to AF detection than the second AF detection criterion, and the second AF detection criterion has greater specificity to AF detection than the first AF detection criterion. The control circuit is configured to initiate storing in the memory of sampled values of a segment of the cardiac signal that includes the episode of AF when the episode of AF is detected by both the first AF detection criterion and the second AF detection criterion.

This section is intended to provide a brief overview of subject matter of the present patent application. It is not intended to provide an exclusive or exhaustive explanation of the invention. The detailed description is included to provide further information about the present patent application such as a discussion of the dependent claims and the interrelation of the dependent and independent claims in addition to the statements made in this section.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, the various examples discussed in the present document.

DETAILED DESCRIPTION

An ambulatory medical device can include one or more of the features, structures, methods, or combinations thereof described herein. For example, a cardiac monitor or a cardiac stimulator may be implemented to include one or more of the advantageous features or processes described below. It is intended that such a monitor, stimulator, or other ambulatory device need not include all of the features described herein, but may be implemented to include selected features that provide for unique structures or functionality. Such a device may be implemented to provide a variety of therapeutic or diagnostic functions.

Figure 1:
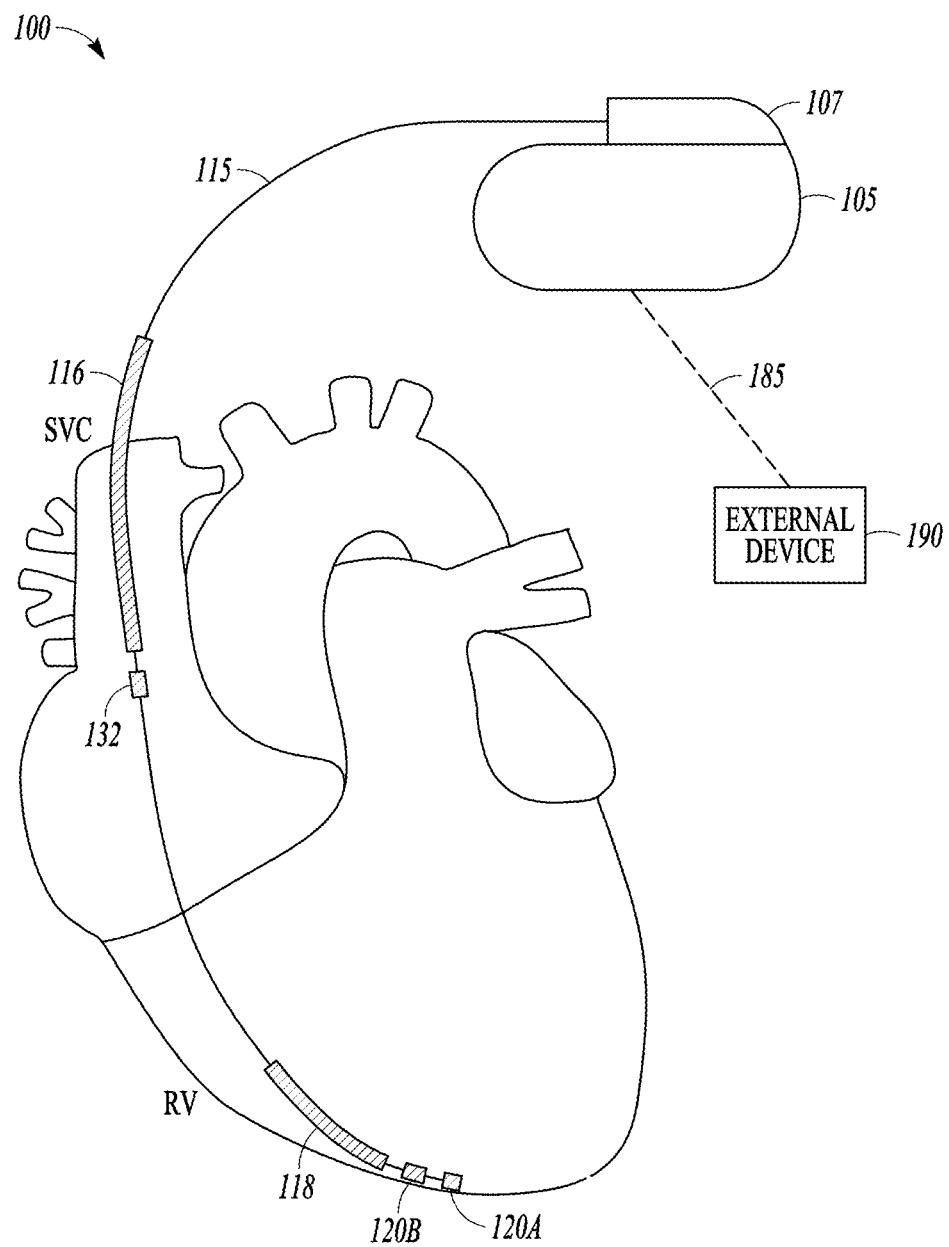
FIG. 1 is an illustration of an example of portions of a medical device system that includes an IMD.

FIG. 1 is an illustration of an example of portions of a system 100 that includes an ambulatory medical device that is an IMD 105. Examples of the IMD 105 include, without limitation, a pacemaker, a cardioverter, a defibrillator, and other cardiac monitoring and therapy delivery devices, including cardiac devices that include or work in coordination with one or more neuro-stimulating devices, drugs, drug delivery systems, or other therapies. In an example, the system 100 shown is used to treat a cardiac arrhythmia. The IMD 105 typically includes an electronics unit coupled by one or more cardiac leads 115 to a heart of a patient or subject. The electronics unit of the IMD 105 typically includes components that are enclosed in a hermetically-sealed housing sometimes referred to as a canister or "can." The system 100 also typically includes an IMD programmer or other external system 190 that communicates one or more wireless signals 185 with the IMD 105, such as by using radio frequency (RF) or by one or more other telemetry methods.

The example shown includes a right ventricular (RV) lead 115 having a proximal end and a distal end. The proximal end is coupled to a header connector 107. The distal end is configured for placement in the RV. The RV lead 115 can include one or more of a proximal defibrillation electrode 116, a distal defibrillation electrode 118 (e.g., RV Coil), an RV tip electrode 120A, and an RV ring electrode 120B. The defibrillation electrode 116 is generally incorporated into the lead body such as in a location suitable for supraventricular placement in the superior vena cava (e.g., SVC Coil). In some examples, the RV lead 115 includes a ring electrode 132 (e.g., SVC ring) in the vicinity of the proximal defibrillation electrode 116. The defibrillation electrode 118 is incorporated into the lead body near the distal end, such as for placement in the RV. The RV electrodes 120A and 120B can form a bipolar electrode pair and are generally incorporated into the lead body at the lead distal end. The electrodes 116, 118, 120A, and 120B are each electrically coupled to IMD 105, such as through one or more conductors extending within the lead body. The proximal defibrillation electrode 116, distal defibrillation electrode 118, or an electrode formed on the can of IMD 105 allow for delivery of cardioversion or defibrillation pulses to the heart. The RV tip electrode 120A, RV ring electrode 120B, or an electrode formed on the can of IMD 105 allow for sensing an RV electrogram signal representative of RV depolarizations and delivering RV pacing pulses. The IMD 105 includes a sense amplifier circuit to provide amplification or filtering of the sensed signal. Sensing and pacing allows the IMD 105 to adjust timing of the heart chamber contractions.

Some IMDs, such as shown in FIG. 1, may not include any electrodes for sensing electrical activity in an atrium. For example, the IMD 105 can be an ICD with single ventricular chamber sensing. The ICD can include an electrode attached to a single ventricular lead, and use intrinsic cardiac signals sensed with the ventricular electrode for arrhythmia detection and discrimination (e.g., by rate sensing and/or depolarization signal morphology analysis).

An IMD may be a diagnostic-only device and not provide electrical therapy to the patient. Such a device may include a combination of the RV tip electrode 120A, RV ring electrode 120B, or the electrode formed on the can of IMD 105 allow for sensing ventricular depolarizations. Note that the specific arrangement of leads and electrodes are shown the illustrated example of FIG. 1 is intended to be non-limiting.

Figure 2:
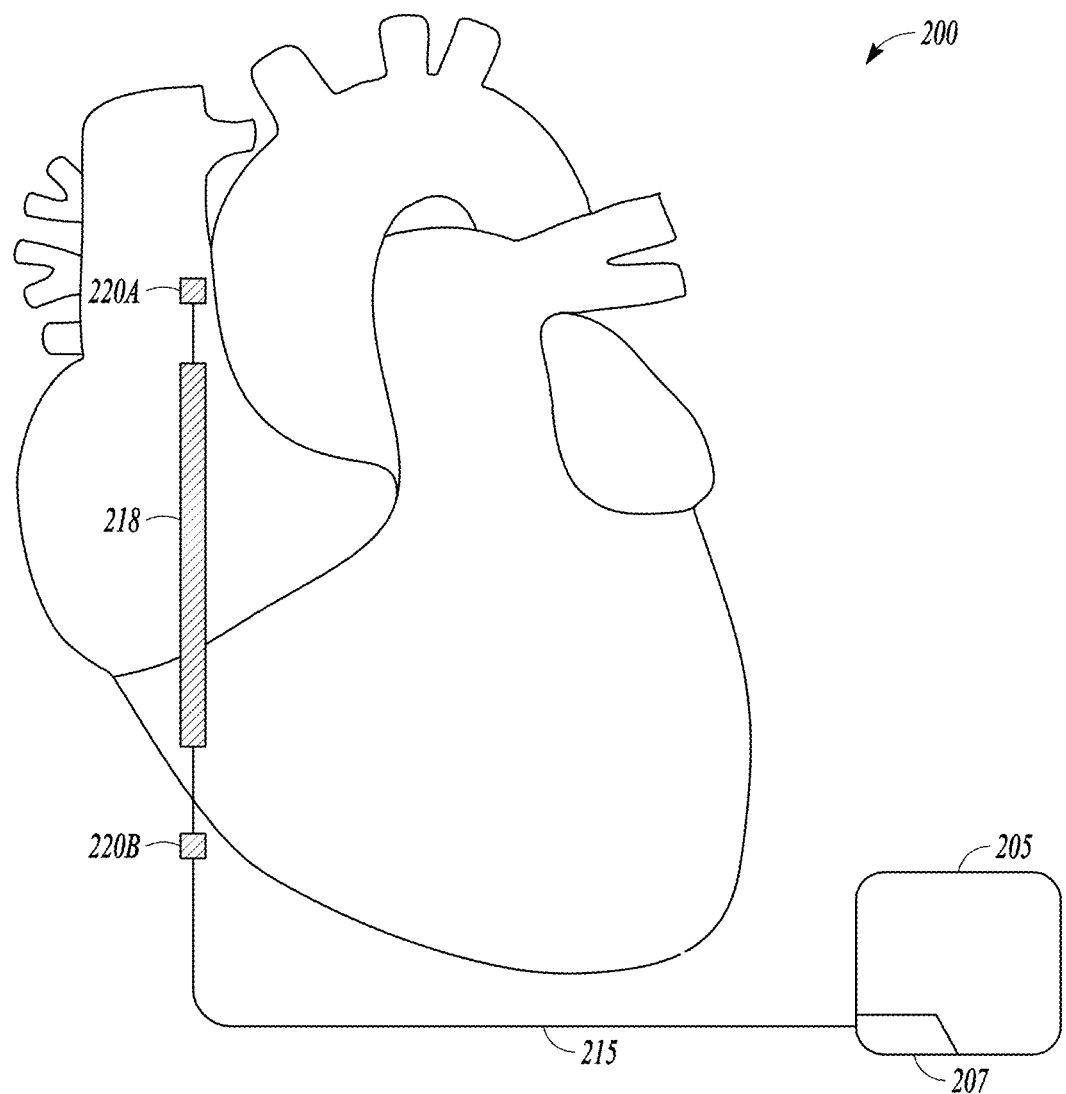
FIGS. 2 and 3 are illustrations of further examples of an IMD.

FIG. 2 is an illustration of another example of portions of a system 200 that includes an S-ICD 205. The S-ICD 205 is implantable subcutaneously and includes a lead 215. The lead 215 is also implanted subcutaneously and the proximal end of the lead 215 is coupled to a header connector 207. The lead 215 can include electrode 220A and electrode 220B to sense ventricular depolarization (e.g., using far-field sensing), but in the example illustrated, the lead does not include any electrodes that directly contact the heart. The lead 215 includes a defibrillation electrode 218 that may be a coil electrode. The S-ICD 205 may provide one or more of cardioversion therapy and defibrillation high energy shock therapy to the heart using the defibrillation electrode 218 and an electrode formed on the can of the S-ICD 205. In some examples, the S-ICD 205 may also provide pacing pulses for anti-tachycardia therapy or bradycardia therapy. Note that direct atrial sensing is not provided in the arrangement of the electrodes, but electrodes 220A and 220B allow for sensing a far-field ventricular electrogram signal.

Figure 3:
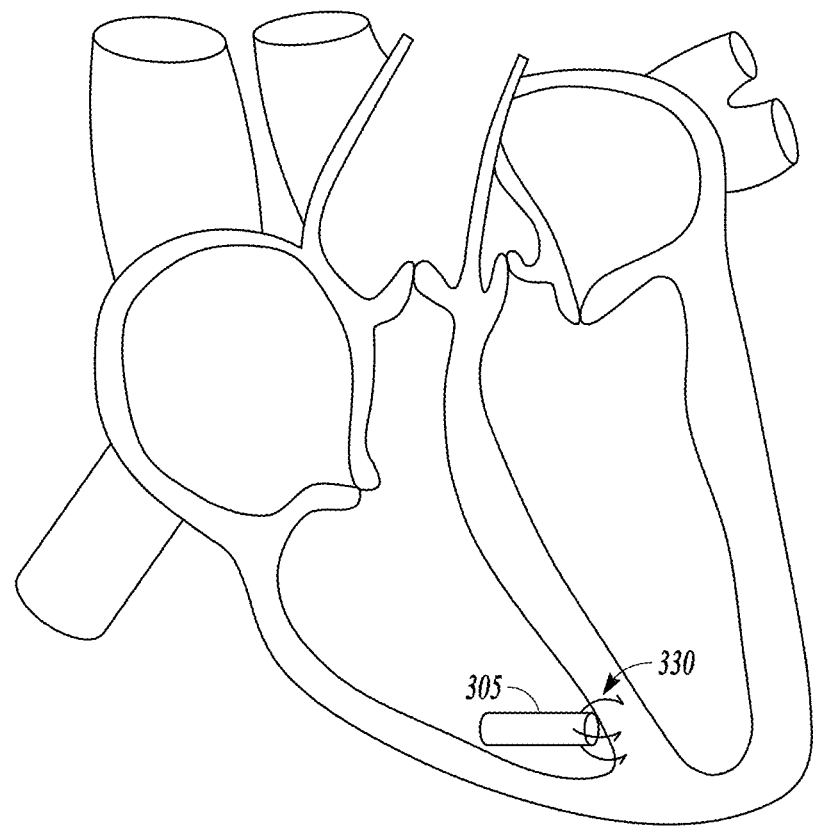

FIG. 3 is an illustration of an example of an IMD that is leadless. In the example shown, the IMD is a leadless pacemaker 305. The leadless pacemaker 305 is shown positioned at the endocardium within a ventricular chamber, but the leadless pacemaker 305 may be positioned at other locations of the heart. The leadless pacemaker 305 example has a cylindrical or bullet shape housing and may include one or more electrodes arranged along the cylindrical housing to sense electrical signals of the heart and/or provide electrical stimulation for pacing the heart. The one or more electrodes may be used for communication. The leadless pacemaker 305 may include a mechanism 330 to fix the pacemaker to the myocardium. Examples of the fixation mechanism can include one or more tines, one or more barbed tines, and one or more helix-shaped fixation mechanisms. Direct atrial sensing may not be provided by the electrodes for the device placement shown in the example, but the electrodes may provide an RV electrogram signal.

Other examples of an IMD include an implantable loop recorder (ILR), a diagnostic device without leads in the heart, and a neurostimulator (including but not limited to vagus nerve stimulators, baroreceptor stimulators, and spinal cord stimulators), or other IMD. These types of devices may not include an electrode positioned in the atrium.

Figure 4:
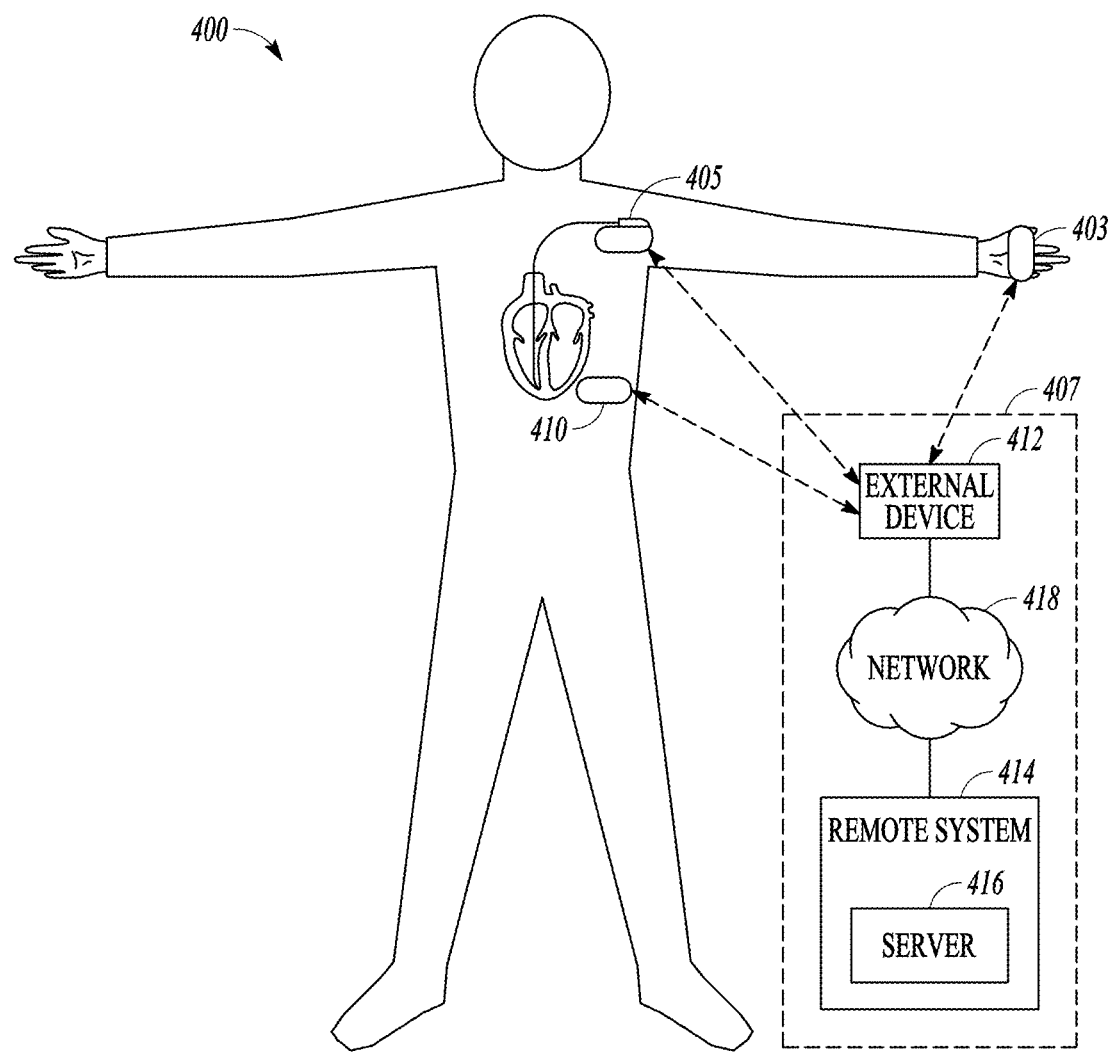
FIG. 4 is an illustration of portions of another example of a medical device system.

FIG. 4 is an illustration of portions of another example of a medical device system 400. The system 400 may include one or more ambulatory medical devices, such as a conventionally implantable or subcutaneously implantable medical device 405, a wearable medical device 410, or a handheld medical device 403. One or more of the medical devices can include a communication circuit (e.g., a telemetry circuit) to communicate the indication of AF to a communication system 407. The communication system 407 can include an external communication device 412 and a remote system 414 that communicates with the external communication device 412 via a network 418 (e.g., the internet, a proprietary computer network, or a cellular phone network). The remote system 414 may include a server 416 remotely located from the external communication device 412 and the subject to perform patient management functions. The external communication device 412 may include a programmer to program therapy parameters of a device-based therapy provided by the implantable medical device. One or both of the external communication device 412 and the remote system 414 may include a display to present the indication of AF to a user, such as a clinician.

Figure 5:
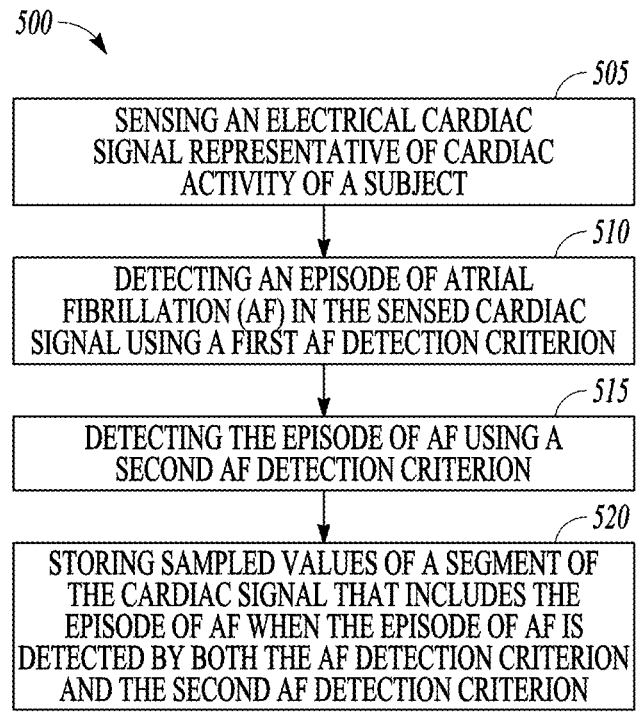
FIG. 5 shows a flow diagram of an example of a method of operating an ambulatory medical device.

FIG. 5 is a flow diagram of an example of a method 500 of operating an ambulatory medical device. The method 500 provides for detecting AF using the ambulatory medical device even though the ambulatory medical device may not include electrodes and sensing circuitry to implement direct atrial sensing and recording a detected episode of AF.

At 505, an electrical cardiac signal representative of cardiac activity of a subject is sensed using the ambulatory medical device. In some examples, the cardiac signal can include information corresponding to ventricular depolarization intervals (or V-V intervals) of a subject.

At 510, an episode of AF is detected in the sensed cardiac signal using a first AF detection criterion, and at 515 the episode of AF is detected or redetected using a second AF detection criterion. Thus, the AF detection can be two-tiered. The first AF detection criterion may have greater sensitivity to AF detection than the second AF detection criterion, and the second AF detection criterion has greater specificity to AF detection than the first AF detection criterion. Sensitivity refers to the ability of the detection scheme of a device to effectively detect an abnormal heart rhythm that the device may treat (e.g., AF). Specificity refers to the ability of the detection scheme of a device to correctly identify heart rhythm that the device is not intended to treat (e.g., normal rhythms, arrhythmias other than AF, or noise mistakenly identified as cardiac arrhythmia).

In some examples, the second AF detection criterion is a different detection method than the first AF detection criterion. In some examples, the second AF detection criterion is the same detection method as the first AF detection criterion, but the thresholds for AF detection are sufficiently different to increase the detection specificity of the second AF detection criterion relative to the first AF detection criterion.

At 520, when the episode of AF is detected by both the first AF detection criterion and the second AF detection criterion, sampled values are stored of the segment of the cardiac signal that includes the detected episode of AF. This allows for storage of an AF electrogram that can be later uploaded for evaluation by a clinician.

Figure 6:
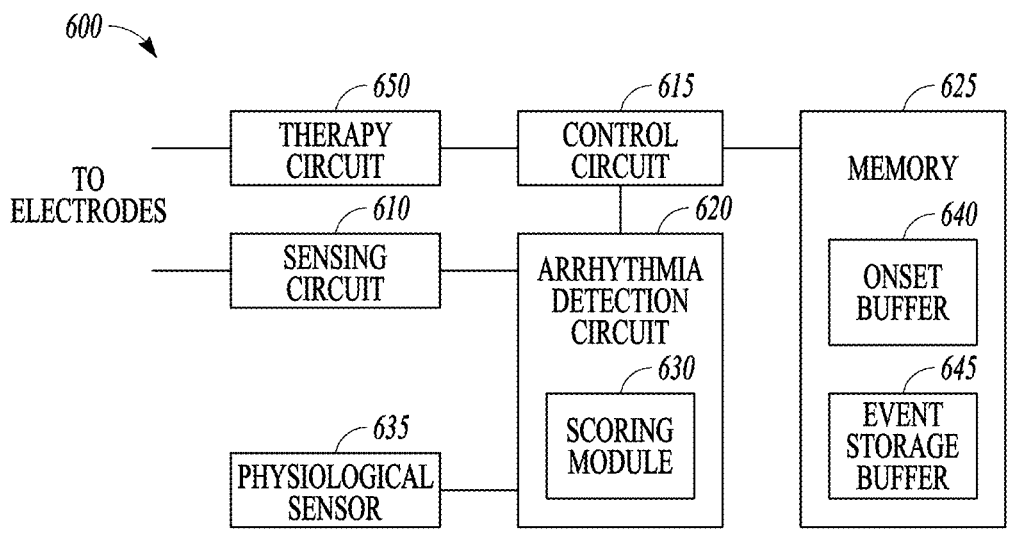
FIG. 6 shows a block diagram of portions of an example of an ambulatory medical device.

FIG. 6 shows a block diagram of portions of an example of an ambulatory medical device. The device 605 includes a sensing circuit 610, a control circuit 615, an arrhythmia detection circuit 620, and may include a memory 625. The sensing circuit 610 may generate a sensed cardiac signal representative of cardiac activity of a subject. In certain examples, the sensing circuit 610 may be electrically coupled to one or more implantable electrodes included in a lead arranged for placement in a heart chamber. In certain examples, the sensing circuit 610 may be electrically coupled to one or more implantable electrodes included in a leadless implantable medical device. In certain examples, the sensing circuit 610 may be electrically coupled to one or more implantable electrodes configured to sense cardiac signals without direct cardiac contact with the subject (e.g., a subcutaneously implantable electrode). In certain examples, the sensing circuit 610, the control circuit 615, the arrhythmia detection circuit 620, and the memory 625 are included in a wearable device or a handheld device. In variations the memory can be included in a separate device or can be a central memory located in a network "cloud."

The control circuit 615 may include a microprocessor, a digital signal processor, application specific integrated circuit (ASIC), or other type of processor, interpreting or executing instructions included in software or firmware. The memory 625 may be integral to or separate from the control circuit 615. The arrhythmia detection circuit 620 may also be integral to the control circuit 615 or may be separate from the control circuit 615. In certain examples, the sensing circuit 610 is included in a first device and the arrhythmia detection circuit and the control circuit are included in a second separate device. In certain examples, the first device is implantable and the second devices is external.

The arrhythmia detection circuit 620 detects an episode of AF in the sensed cardiac signal using a first AF detection criterion and detects the episode of AF using a second AF detection criterion. In response to the AF detection by both the first AF detection criterion and the second AF detection criterion, the control circuit 615 initiates or triggers the storing (e.g., in memory 625 or a different memory) of sampled values of a segment of the cardiac signal that includes the episode of AF.

Figure 7:
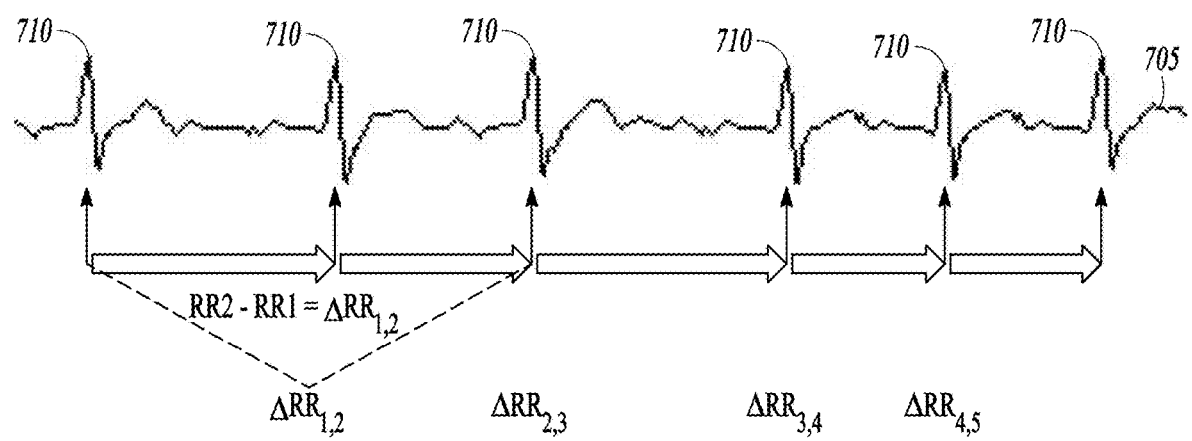
FIG. 7 shows a representation of a sensed cardiac signal.

According to some examples, the first AF detection criterion is a measure of ventricular depolarization (V-V) interval dispersion. FIG. 7 shows a representation of a sensed cardiac signal 705. The signal is shown having a number of R-waves 710. The V-V intervals can be determined as intervals between R-waves. RR1 in the Figure refers to the first interval between the first two R-waves; RR2 is the second interval between the second R-wave and the third R-wave, and so on. Differences between the V-V intervals are referred to $\Delta RR_{1,2}$ (e.g., the difference between the RR2 and RR1), $\Delta RR_{2,3}$, and so on.

Figure 8:
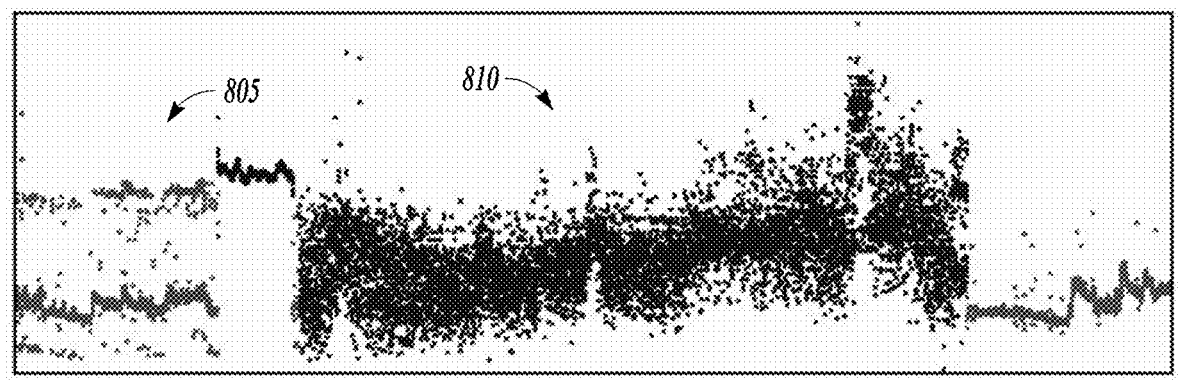
FIG. 8 shows an example of a sensed physiological signal having both normal sinus rhythm and atrial fibrillation.

FIG. 8 shows an example of a sensed physiological signal having a first region 805 corresponding to NSR and a second region 810 corresponding to AF. In the NSR region, the V-V intervals will be more regular and the differences in the V-V intervals will be small. In the AF region, the V-V intervals will be more scattered and the values of the differences in the V-V intervals will be more varied than for NSR.

In some examples, the arrhythmia detection circuit 620 determines ventricular depolarization (V-V) intervals using the sensed physiological signal and monitors information corresponding to the V-V intervals. The arrhythmia detection circuit 620 may include a peak detector circuit to detect R-waves in the sensed physiological signal to determine V-V intervals. The arrhythmia detection circuit 620 may sample the V-V intervals and store the samples in device memory 625 or a different memory. The arrhythmia detection circuit 620 may determine differences between the V-V intervals and determine a measure of V-V interval dispersion using the determined V-V interval differences.

In some examples, the measure of V-V interval dispersion includes a determined variance of the determined interval differences. As the first AF detection criterion, the arrhythmia detection circuit 620 may compare the determined variance to a specified variance threshold value and generate an indication of AF when the determined variance satisfies the specified variance threshold value.

Other measures of ventricular interval dispersion can be used as the first AF detection criterion. In some examples, the arrhythmia detection circuit 620 determines the differences in the V-V intervals and classifies the interval differences as one of stable, unstable, or unstable and random. The interval classifications can be used to determine V-V interval dispersion.

In certain variations, the intervals are classified into a stable bin, an unstable bin, or an unstable-random bin. An interval difference may be classified as stable when the interval difference is less than a specified threshold difference value from an immediately previous interval difference. An interval difference may be classified as unstable when the interval difference is more than the specified threshold difference value from the immediately previous interval difference, and classified as unstable-random when the magnitude of the interval difference is more than the specified threshold difference value from the immediately previous interval difference and the interval difference is a negative value, that satisfies a specified negative value threshold.

In certain examples, the threshold difference value is a value corresponding to less than a 10 bpm difference in rate between the two intervals. Thus, if RR2 in FIG. 7 is 1000 ms corresponding to 60 bpm, and RR1 is 857 ms corresponding to 70 bpm, the interval difference $\Delta RR_{1,2}$ is binned as stable. If RR1 is less than 857 ms, then the interval difference is binned as unstable. If RR2 is less than 857 ms and RR1 is equal to 1000 ms, the interval difference $\Delta RR_{1,2}$ is binned as unstable-random. In certain examples, interval differences are only considered for binning if the intervals used (e.g., interval RR1 and RR2) are included in a triplet of three ventricular beats that are longer than a specified minimum interval (e.g., an interval of 324 ms corresponding to a heart rate of 185 bpm).

In the example of FIG. 8, more of the V-V interval differences will be stable in the NSR region. In the AF region, the number of unstable V-V interval differences and unstable-random V-V interval differences will increase relative to the number of stable V-V interval differences. The arrhythmia detection circuit 620 may determine a first metric of ventricular interval dispersion using a number of stable interval differences and a number of unstable interval differences. The first metric may include a first ratio determined using a number of stable interval differences and a number of unstable interval differences (e.g., first ratio=unstable/stable).

Returning to the device 605 of FIG. 6, the arrhythmia detection circuit 620 may determine a second metric of ventricular interval dispersion using a determined portion of the interval differences that are unstable-random. The second metric may include a second ratio determined using a number of unstable-random interval differences and a sum including the number of stable interval differences and the number of unstable interval differences (e.g., second ratio= (unstable-random)/(stable+unstable)).

In the case where the first and second metrics are the ratios, the value of the first ratio will increase in the presence of AF because the number of V-V intervals classified as unstable will increase. The value of the second ratio will tend to increase in the presence of AF because the number of V-V intervals differences classified as unstable-random will increase.

As the first AF detection criterion, the arrhythmia detection circuit 620 may compare the determined first ratio to a specified first ratio threshold value (e.g., a ratio value of 3) and compare the determined second ratio to a specified second ratio threshold value (e.g., a ratio value of 0.06 or 6%). The arrhythmia detection circuit 620 generates the indication of AF when the first ratio satisfies the specified first ratio threshold value and the determined second ratio satisfies the specified second ratio threshold value.

As the second AF detection criterion, in some examples the arrhythmia detection circuit 620 determines a V-V interval distribution using sampled V-V interval values and determines a heart rate density index (HRDI) as a portion of the sampled V-V interval values corresponding to a V-V interval occurring most often in the distribution.

Figure 9:
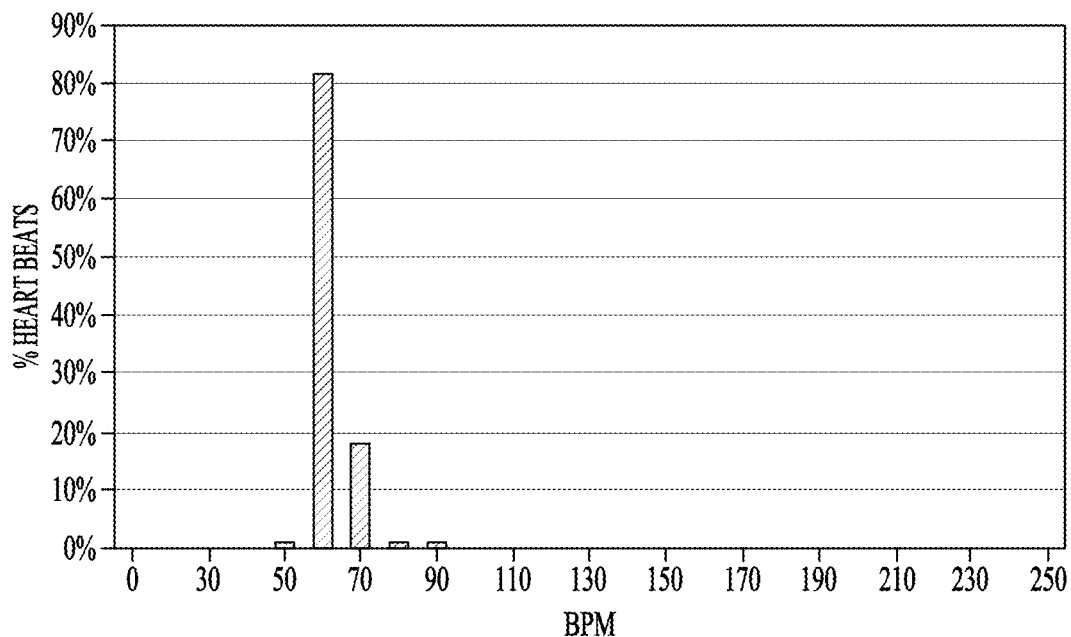
FIG. 9 shows a graph of an example of a heart rate distribution for normal sinus rhythm.
Figure 10:
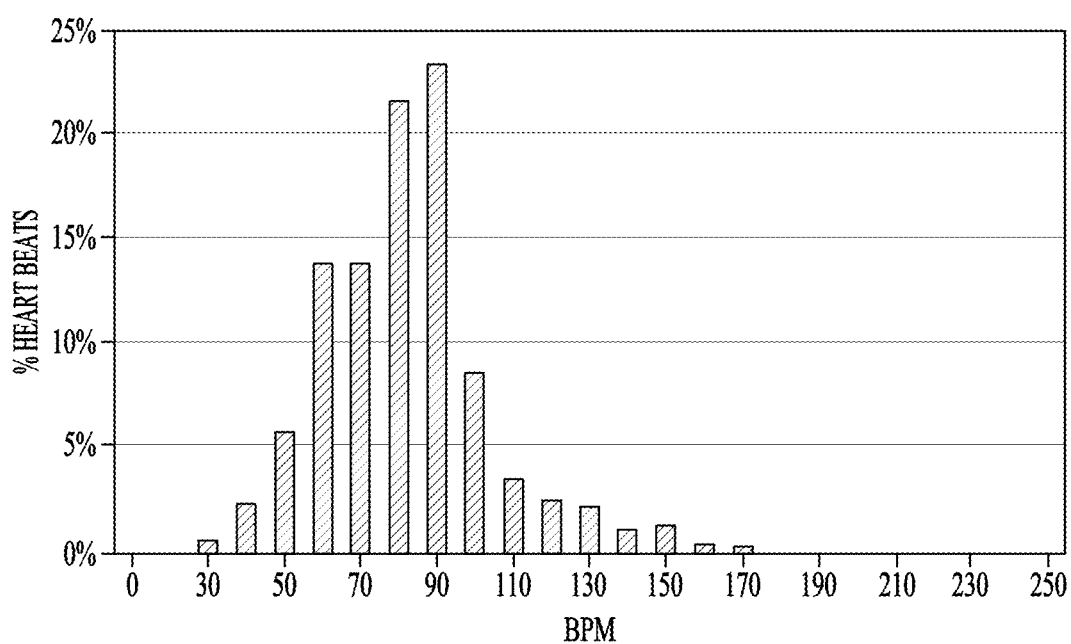
FIG. 10 shows a graph of an example of a heart rate distribution for a patient in atrial fibrillation.

FIG. 9 shows a graph of an example of a heart rate distribution for normal sinus rhythm (NSR). Alternatively, the distribution may be a V-V interval distribution. Most of the samples of the distribution are located between approximately 50 bpm and 90 bpm. In some variations, HRDI can be expressed as a fraction (e.g., a percentage) of the intervals. In the example of FIG. 9, the HRDI is 81% corresponding to the heart rate mode of 60 bpm. FIG. 10 shows a graph of an example of a heart rate distribution for a patient in AF. It can be seen that heart rate is less regular in AF than in NSR. In the example of FIG. 10, the HRDI is approximately 23%.

Returning to the device 605 of FIG. 6, the arrhythmia detection circuit 620 compares the HRDI to a specified HRDI threshold value and generates an indication of AF when the determined HRDI satisfies the HRDI threshold value. In the example of FIG. 8, the arrhythmia detection circuit 620 may generate an indication of AF as the second AF detection criterion when the HRDI is less than 25%.

As explained previously, the first AF detection criterion may have greater sensitivity to AF detection than the second AF detection criterion, and the second AF detection criterion may have greater specificity to AF detection than the first AF detection criterion. The difference in sensitivity and specificity can be implemented by adjusting the thresholds of the first AF detection criterion and the second AF detection criterion. For instance, the specified V-V dispersion threshold value of the first AF detection criterion can be lowered to include more candidate rhythms as AF, and the HRDI of the second AF detection criterion can be lowered to make the second AF detection more difficult to satisfy.

Other methods of AF detection can be used for one or both of the first AF detection criterion and the second AF detection criterion. In some examples, the first AF detection criterion can include determining a heart rate mode. Returning to the heart rate distribution of FIG. 9, the mode for the distribution is approximately 60 bpm because that is the heart rate that appears most often in the distribution. In the example of FIG. 10, the heart rate mode is 90 bpm.

Returning to the device 605 of FIG. 6, the arrhythmia detection circuit 620 may determine a heart rate mode as the heart rate corresponding to a V-V interval value having the most samples in a V-V interval distribution. The arrhythmia detection circuit 620 compares the heart rate mode to a specified heart rate mode threshold value and generates an indication AF when the heart rate mode satisfies the specified heart rate mode threshold value. For instance, the arrhythmia detection circuit 620 may generate an indication of AF when the heart rate mode is an interval of 600 milliseconds (600 ms) or less (corresponding to a heart rate greater than or equal to 100 bpm).

In some examples, one or both of the first AF detection criterion and the second AF detection criterion use morphology of a sensed cardiac signal to detect AF. The arrhythmia detection circuit 620 may include a scoring module 630 that determines a score associated with correlation of the morphology of the sensed cardiac signal to the morphology of a template signal representative of AF. An example of a correlation score is a feature correlation coefficient (FCC). The FCC can provide an indication of a degree of similarity between the shape of the sensed electrogram and the shape of the template electrogram signal that represents AF. The template may be recorded for a particular subject or may be created based on a patient population. An approach to calculating a correlation score can be found in U.S. Pat. No. 7,904,142, titled "Self-Adjusting ECG Morphological Feature Correlation Threshold," filed May 16, 2007, which is incorporated herein by reference in its entirety.

In some examples, arrhythmia detection circuit 620 applies at least one of the first AF detection criterion and the second AF detection criterion to detect an episode of AF using the determined score. AF can be detected when the determined score satisfies a specified threshold score. The detection for AF can be adjusted to be sensitive or less sensitive by adjusting the threshold score.

The values of V-V interval dispersion, heart rate mode, HRDI, and morphology score can be measured only using ventricular sensing. In this way, AF can be detected without including dedicated atrial sensing in the ambulatory medical device. If other sensing circuits are available, other criterion can be used.

In some examples, the device 605 of FIG. 6 includes a physiological sensor circuit 635. The physiological sensor circuit 635 generates a physiological signal that includes physiological information of the subject. During AF, the performance of the subject's hemodynamic system may be degraded. The degraded performance may be reflected in the physiological signal.

An example of the physiological sensor circuit 635 is a pulmonary arterial pressure (PAP) sensor circuit. A PAP sensor circuit may be implanted in a pulmonary artery to sense a PAP signal. Examples of an implantable PAP sensor are described in U.S. Pat. No. 7,566,308, titled "Method and Apparatus for Pulmonary Artery Pressure Signal Isolation," filed on Oct. 13, 2005, which is incorporated herein by reference in its entirety. An episode of AF may result in a reduction in PAP of the subject reflected in the sensed PAP signal. In some examples, the arrhythmia detection circuit 620 applies the second AF detection criterion to the sensed PAP signal to confirm an AF detection using the first AF detection criterion. In certain examples, the second AF detection criterion generates an indication of AF when the PAP as reflected in the PAP signal decreases below a specified PAP threshold value. The first AF detection criterion may be applied to a sensed electrogram signal as described previously herein or may be a criterion applied to the PAP signal, with the detection by the first criterion more sensitive than the detection by the second criterion.

Another example of the physiological sensor circuit 635 is a heart sound sensor circuit. Heart sounds are associated with mechanical vibrations from activity of a patient's heart and the flow of blood through the heart. Heart sounds recur with each cardiac cycle and are separated and classified according to the activity associated with the vibration. The first heart sound (S1) is the vibrational sound made by the heart during tensing of the mitral valve. The second heart sound (S2) marks the beginning of diastole. The third heart sound (S3) and fourth heart sound (S4) are related to filling pressures of the left ventricle during diastole.

The physiological signal can be a heart sound signal representative of one or more heart sounds produced by the heart sound sensor circuit. An example of a heart sound sensor includes an accelerometer or microphone. An approach for measuring heart sounds can be found in U.S. Pat. No. 7,115,096, titled "Method and Apparatus for Monitoring of Diastolic Hemodynamics," filed on Dec. 30, 2002, which is incorporated herein by reference in its entirety.

An episode of AF may result in a change to a heart sound parameter measurable in the heart sound signal. For example, the amplitude of an S1 or S2 heart sound may decrease during an AF episode. In some examples, the arrhythmia detection circuit 620 applies the second AF detection criterion to the sensed heart sound signal to confirm an AF detection using the first AF detection criterion. The first AF detection criterion may be applied to a sensed electrogram signal as described previously herein or may be a criterion applied to the heart sound signal, with the detection by the first criterion more sensitive than the detection by the second criterion. The first AF detection criterion may be applied to a different heart sound parameter than the second AF detection criterion.

As explained previously, in response to the AF detection by both of the first AF detection criterion and the second AF detection criterion, the control circuit 615 initiates the storing in memory 625 of sampled values of a segment of the cardiac signal (e.g., an electrogram) that includes the episode of AF.

Figure 11:
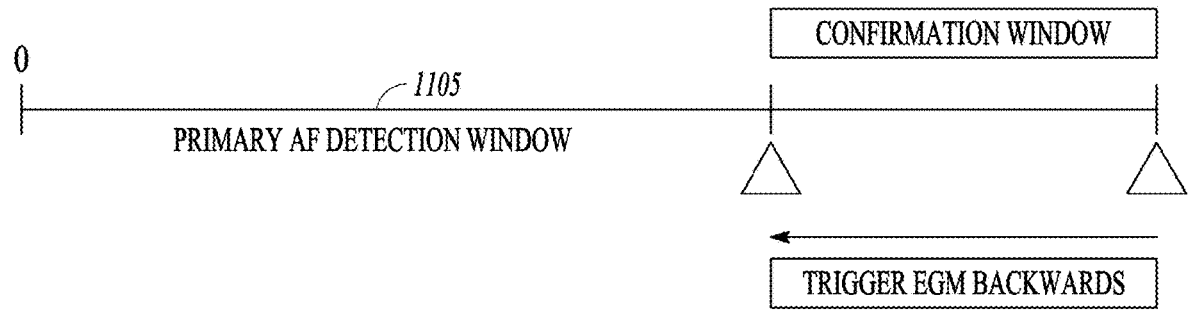
FIG. 11 illustrates an approach to triggering the storing of a cardiac signal in response to detection of atrial fibrillation.

FIG. 11 illustrates an approach to triggering the storing of a cardiac signal in response to detection of AF. The arrhythmia detection circuit 620 applies the first detection criterion during the primary AF detection window 1105. In response to detection of AF using the first AF detection criterion, the control circuit 615 triggers storage of sampled values of the cardiac signal.

The stored samples are represented in FIG. 11 as an AF confirmation window 1110. The arrhythmia detection circuit 620 applies the second AF detection criterion to the stored samples of the cardiac signal. If the arrhythmia detection circuit 620 also detects the episode of AF using the second AF detection criterion, the arrhythmia detection circuit 620 generates an indication of the detection of AF. The indication may be a signal communicated to the control circuit 615, and the control circuit 615 continues to store the sampled values of the cardiac signal in response to the generated indication of AF. The samples stored in the AF confirmation window and the subsequent samples may be stored in memory 625.

This can be useful to upload the cardiac signal with the confirmation of the episode of AF for analysis. If AF is not detected by the second AF detection criterion during the AF confirmation window, the control circuit 615 may terminate the storing of the cardiac signal and return to searching the cardiac signal for AF using the first AF detection criterion.

Figure 12:
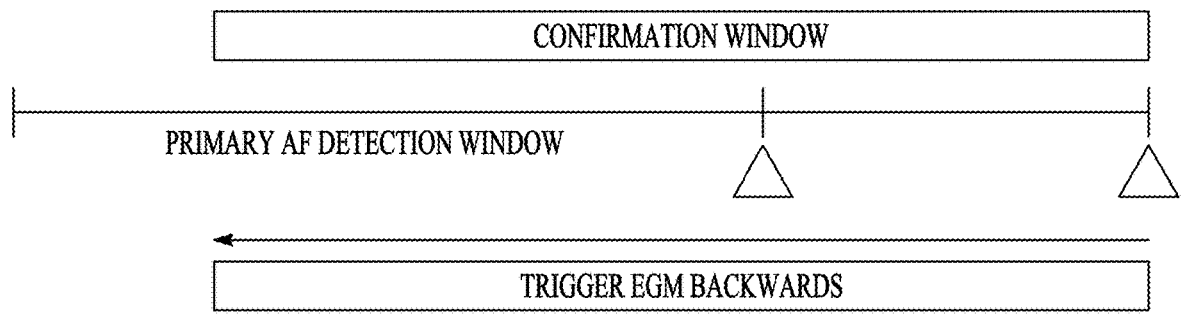
FIG. 12 illustrates an example of another approach to triggering the storing of a cardiac signal in response to detection of atrial fibrillation.

FIG. 12 illustrates an example of another approach to triggering the storing of a cardiac signal in response to detection of AF. The memory 625 includes a first onset buffer 640 and a second event storage buffer 645. The buffers may be in separate memory or may be in different areas of the same memory. The control circuit 615 may initiate storing sampled values of the sensed cardiac signal in the onset buffer, which can be used as a primary AF detection window. The arrhythmia detection circuit 620 may apply both the first AF detection criterion and the second AF detection criterion to the cardiac signal segment stored in the onset buffer 640.

If no AF events are detected, the control circuit 615 may initiate overwriting the onset buffer. If AF is detected using the first and second detection criteria, the control circuit 615 may initiate the moving of the onset buffer contents to the event storage buffer 645 and storage of subsequently sampled values of the sensed cardiac signal. The event storage buffer 645 may include representations of both the onset of AF and the confirmation of AF.

In some examples, if the control circuit 615 determines that no sampled values of a segment of the cardiac signal have been stored for a specified period of time because AF fails to be detected by both the first and the second criteria, the control circuit may initiate the storing in the memory of sampled values of a segment of the cardiac signal that includes the episode of AF when the episode of AF is detected only by the first AF detection criterion. This provides for storing of an electrogram showing AF detection by the first AF detection criterion and non-detection by the second AF detection criterion. This may be useful to allow review of the electrogram to adjust the detection of one or both AF detection criteria.

In some examples, the arrhythmia detection circuit 620 applies the first AF detection criterion to the contents of the onset buffer 640. If an AF event is detected, the contents of the onset buffer are moved to the event storage buffer. The arrhythmia detection circuit 620 applies the second AF detection criterion to the contents of the event storage buffer to confirm AF.

Figure 13:
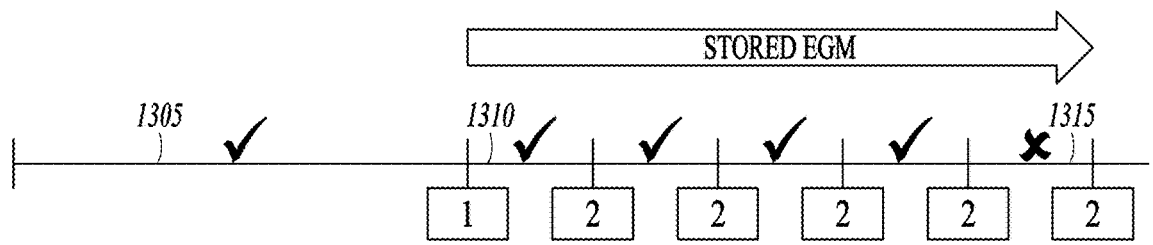
FIG. 13 illustrates an example of still another approach to triggering the storing of a cardiac signal in response to detection of atrial fibrillation.

FIG. 13 illustrates an example of still another approach to triggering the storing of a cardiac signal in response to detection of AF. The arrhythmia detection circuit 620 applies the first AF detection criterion during an initial primary AF detection window 1305. The first AF detection criterion may be applied in real time to the sensed cardiac signal or may be applied to sampled values of the sensed cardiac signal stored in an onset buffer 640. When AF is detected using the first AF detection criterion, the control circuit 615 initiates storing of the sampled values of the cardiac signal. In certain variations, the control circuit 615 initiates storing of the sampled values in event storage buffer 645.

The arrhythmia detection circuit 620 applies the second AF detection criterion to the stored sampled values of the sensed cardiac signal. The second AF detection criterion is applied for a secondary detection window 1310. The secondary detection window may have a time duration less than the time duration of the primary detection window. The control circuit 615 continues to store sampled values for the cardiac signal when AF is detected using the second AF detection criterion. When AF is not detected using the second AF detection criterion (e.g., at window 1315), the control circuit 615 terminates storing of the sampled values for the cardiac signal.

An ambulatory medical device may use different combinations of the examples of AF detection described. A medical device system (e.g., the system of FIG. 4) may be used to present a menu (e.g., using a graphical user interface or GUI) to a user to select from available AF detection options.

Figure 14:
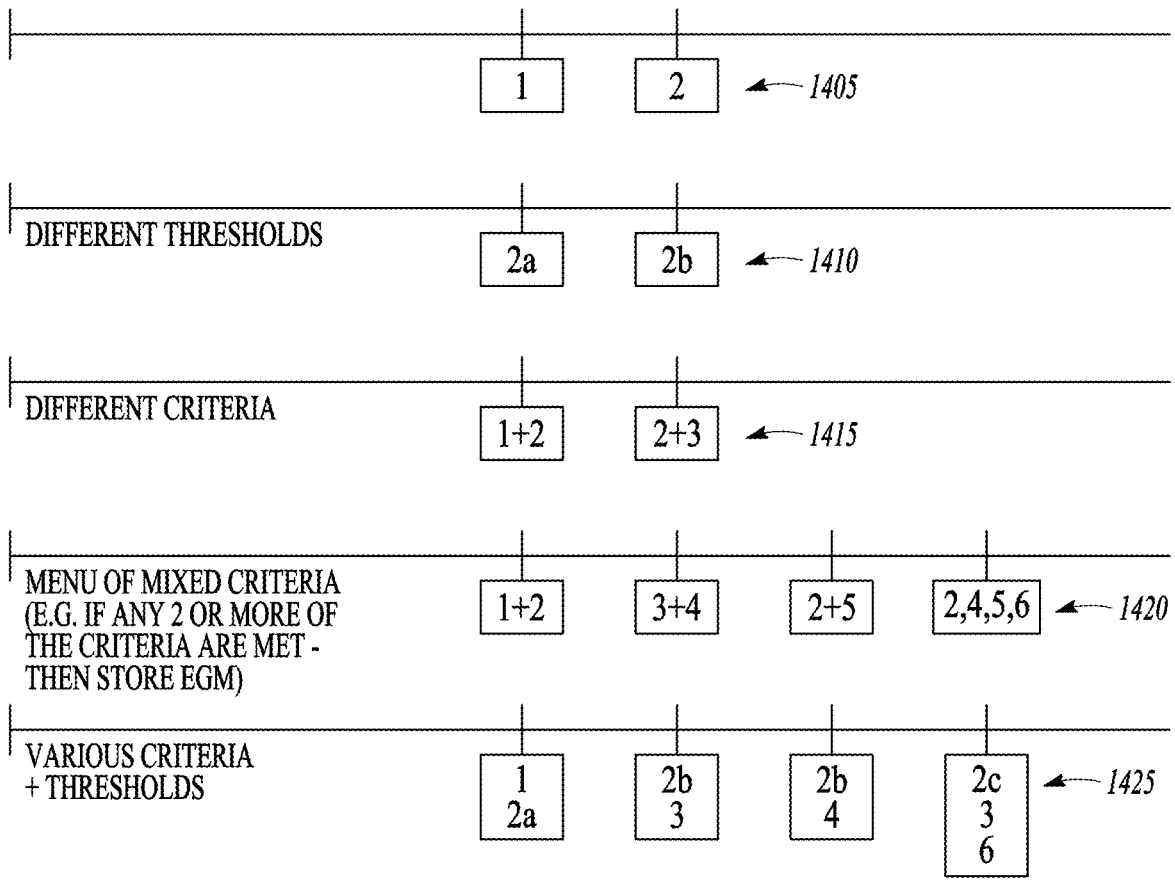
FIG. 14 shows an example of a menu of different options available for atrial fibrillation detection.

FIG. 14 shows an example of different options available for AF detection. The options may be available for a user to enable (e.g., using GUI), or may be pre-programmed into the medical device system. Option 1405 shows the case where the ambulatory medical device is configured with a first AF detection criterion that uses a different detection method than a second AF detection criterion. The first and second AF detection criteria (denoted as methods 1 and 2 in FIG. 14) may include any combination of the detections methods described previously herein, such as V-V interval dispersion, HRDI, heart rate mode, heart sounds, PAP, and morphology correlation. Option 1410 shows the case where the first and second AF detection criteria use the same AF detection method (denoted as method 2), but different thresholds (denoted as thresholds a, b) are used for AF detection.

Option 1415 shows the case where different combinations of AF detection criteria are used to detect AF. In some examples, the AF detection may involve two tiers of detection. A combination of two detection methods is used as a first tier. For instance, the two detection methods may include V-V interval dispersion and HRDI. The second tier of detection uses a combination of HRDI and heart sound measurements. In some examples, the AF detection only involves one tier of detection, and AF may be detected when AF is detected using either of the first combination or the second combination of criteria. The control circuit may initiate storing sampled values of a cardiac signal when AF is detected using one or both of the first and second tiers of AF detection.

Option 1420 shows the case where six AF detection criteria are available for selection. The ambulatory medical device may be programmed to detect AF and initiate storing sampled values of a cardiac signal when any combination of two or more detection criteria is satisfied. Option 1425 shows the case where different AF detection criteria can be enabled and also different detection thresholds for the criteria can be enabled. The ambulatory medical device may detect AF when automatically determining that any combination of the AF detection criteria and detection thresholds has been satisfied.

In certain examples, a user selects different AF detection criteria and also selects different detection thresholds for the criteria. Providing a medical device or medical device system that provides different selectable combinations criteria for AF detection allows a clinician to tune the triggering of AF electrograms for an individual patient for that patient's individual needs. This can result in the storing of AF electrograms for later uploading and evaluation by a clinician that are most relevant to the patient's condition.

Figure 15:
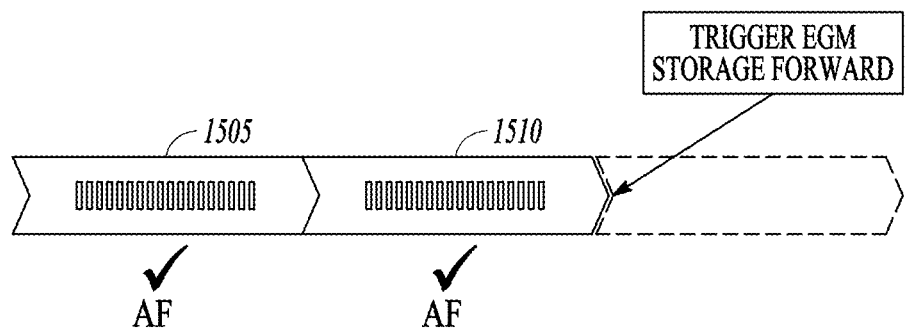
FIG. 15 illustrates an example of still another approach to triggering the storing of a cardiac signal in response to atrial fibrillation detection.

FIG. 15 illustrates still another example of another approach to triggering the storing of a cardiac signal in response to detection of AF. In this example, the arrhythmia detection circuit 620 applies the same AF detection criterion during a first AF detection window 1505 and a second consecutive AF detection window 1510. The AF detection criterion can be any of the detections methods described previously herein, such as V-V interval dispersion, HRDI, heart rate mode, heart sounds, PAP, and morphology correlation. The control circuit 615 triggers storage of sampled values of the sensed cardiac signal in response to detecting AF during both the first and second consecutive detection windows.

Returning to FIG. 6, as explained previously the device 605 may be a diagnostic-only device. In some examples, the device 605 provides a therapy to the subject. The device may include a therapy circuit 650 that can be electrically coupled to electrodes to provide an anti-arrhythmic cardiac therapy to the subject. The control circuit 615 initiates delivery of an anti-arrhythmic therapy in response to the indication of AF generated by the arrhythmia detection circuit 620.

ADDITIONAL DESCRIPTION AND EXAMPLES

Example 1 includes subject matter (such as an apparatus) comprising a sensing circuit configured to generate a sensed cardiac signal representative of cardiac activity of a subject, an arrhythmia detection circuit electrically coupled to the sensing circuit, a memory, and a control circuit. The arrhythmia detection circuit is configured to: detect an episode of atrial fibrillation (AF) in the sensed cardiac signal using a first AF detection criterion; and detect the episode of AF using a second AF detection criterion. The first AF detection criterion has greater sensitivity to AF detection than the second AF detection criterion, and the second AF detection criterion has greater specificity to AF detection than the first AF detection criterion. The control circuit is configured to trigger storage of sampled values of a segment of the cardiac signal that includes the episode of AF when the episode of AF is detected by both the first AF detection criterion and the second AF detection criterion.

In Example 2, the subject matter of Example 1 optionally includes an arrhythmia detection circuit is configured to: monitor information corresponding to ventricular depolarization (V-V) intervals, determine a V-V interval distribution using sampled V-V interval values, and is further configured to, according to the second AF detection criterion, determine a heart rate density index (HRDI) as a portion of the sampled V-V interval values corresponding to a V-V interval occurring most often in the distribution, compare the HRDI to a specified HRDI threshold value, and generate an indication of AF when the determined HRDI satisfies the HRDI threshold value.

In Example 3 the subject matter of one or both of Examples 1 and 2 optionally includes arrhythmia detection circuit that, according to the first AF detection criterion, is configured to determine a heart rate mode as the heart rate corresponding to a V-V interval value having most samples in the V-V interval distribution, compare the heart rate mode to a specified heart rate mode threshold value, and generate an indication of AF when the heart rate mode satisfies the specified heart rate mode threshold value.

In Example 4, the subject matter of one or any combination of Examples 1-3 optionally includes an the arrhythmia detection circuit that, according to the first AF detection criterion, is configured to determine differences between the V-V intervals, determine a measure of V-V interval dispersion using the determined V-V interval differences; compare the measure of V-V interval dispersion to a specified dispersion threshold value, and generate an indication of AF when the determined measure of V-V dispersion satisfies the specified dispersion threshold value.

In Example 5, the subject matter of one or any combination of Examples 1-4 optionally includes a physiological sensor circuit configured to generate a physiological signal that includes physiological information of the subject, wherein the arrhythmia detection circuit is configured to apply the second AF detection criterion to the sensed physiological signal to detect the episode of AF.

In Example 6, the subject matter of Example 5 optionally includes a physiological sensor circuit that includes at least one of a heart sound sensor circuit and a pulmonary arterial pressure sensor circuit.

In Example 7, the subject matter of one or any combination of Examples 1-6 optionally includes a scoring module configured to determine a score associated with correlation of morphology of the sensed cardiac signal to morphology of a template signal representative of AF, and wherein the arrhythmia detection circuit is configured to apply at least one of the first AF detection criterion and the second AF detection criterion to detect an episode of AF using the determined score.

In Example 8, the subject matter of one or any combination of Examples 1-7 optionally includes a memory that includes a first onset buffer and a second event storage buffer, and wherein the control circuit is configured to: store sampled values of the sensed cardiac signal in the onset buffer and overwrite sampled values previously stored in the onset buffer; and initiate, in response to the AF detection by the first and second AF detection criterion, storing of the sampled values stored in the onset buffer in the event storage and storing subsequently sampled values of the sensed cardiac signal in the event storage buffer.

In Example 9, the subject matter of one or any combination of Examples 1-8 optionally includes a control circuit configured to store sampled values of the cardiac signal in the memory in response to detecting the episode of AF using the first AF detection criterion, wherein the arrhythmia detection circuit is configured to detect the episode of AF using the second AF detection criterion using the stored sampled values of the cardiac signal and generate an indication of the detection of AF, and wherein the control circuit is further configured to continue the storing of the sampled values of the cardiac signal in response to the generated indication of AF.

In Example 10, the subject matter of one or any combination of Examples 1-9 optionally includes a control circuit configured to store sampled values for a first segment of the cardiac signal in the memory for a first time duration in response to the arrhythmia detection circuit detecting the episode of AF using the first AF detection criterion. The arrhythmia detection circuit is configured to apply the second AF detection criterion to the stored values of the first cardiac signal segment, the control circuit is configured to store sampled values for one or more cardiac signal segments having a second time duration less than the first duration when AF is detected by both the first AF detection criterion and the second AF detection criterion. The arrhythmia circuit is optionally configured to apply the second AF detection criterion to the one or more cardiac signal segments having the second time duration, and the control circuit is optionally configured to continue to store sampled values for cardiac signal segments of the second time duration when the arrhythmia detection circuit continues to detect AF in the one or more cardiac signal segments having the second time duration.

In Example 11, the subject matter of one or any combination of Examples 1-10 optionally includes a control circuit configured to determine that no sampled values of a segment of the cardiac signal have been stored for a specified period of time and, in response to the determination, initiate the storing in the memory of sampled values of a segment of the cardiac signal that includes the episode of AF when the episode of AF is detected only by the first AF detection criterion.

In Example 12, the subject matter of one or any combination of Examples 1-11 optionally includes a therapy circuit configured for coupling to electrodes to provide an anti-arrhythmic cardiac therapy to a subject, and a control circuit configured to initiate delivery of an anti-arrhythmic therapy in response to the generated indication of AF.

In Example 13, the subject matter of one or any combination of Examples 1-12 optionally includes a sensing circuit configured to be coupled to at least one of an implantable electrode configured for placement in a heart chamber or a subcutaneously implantable electrode that is configured to sense cardiac signals without direct cardiac contact with the subject.

In Example 14, the subject matter of one or any combination of Examples 1-13 optionally includes a sensing circuit and an arrhythmia detection circuit are included in a wearable device or a handheld device.

Example 15 optionally includes subject matter (such as a system), or can optionally be combined with the subject matter of one or any combination of Examples 1-14 to include such subject matter, comprising a first device configured for sensing an electrical cardiac signal representative of cardiac activity of a subject; and a second device configured for detecting an episode of atrial fibrillation (AF) in the sensed cardiac signal using a first AF detection criterion; detecting the episode of AF using a second AF detection criterion, wherein the first AF detection criterion has greater sensitivity to AF detection than the second AF detection criterion, and the second AF detection criterion has greater specificity to AF detection than the first AF detection criterion; and storing sampled values of a segment of the cardiac signal that includes the episode of AF when the episode of AF is detected by both the first AF detection criterion and the second AF detection criterion.

In Example 16, the subject matter of example 15 optionally includes the second device configured for sampling values of ventricular depolarization (V-V) intervals. The second AF detection criterion optionally includes: determining a V-V interval distribution using sampled V-V interval values; determining a heart rate density index (HRDI) as a portion of the sampled V-V interval values corresponding to a V-V interval occurring most often in the distribution; comparing the HRDI to a specified HRDI threshold value; and generating an indication of AF when the determined HRDI satisfies the HRDI threshold value.

In Example 17, the subject matter of one or both of Examples 15 and 16 optionally includes the second device configured for sampling values of ventricular depolarization (V-V) intervals. The first AF detection criterion optionally includes: determining differences between the monitored V-V intervals; determining a measure of V-V interval dispersion using the determined V-V interval differences; comparing the measure of V-V interval dispersion to a specified dispersion threshold value; and generating an indication of AF when the determined measure of V-V dispersion satisfies the specified dispersion threshold value.

Example 18 includes subject matter (such as an apparatus), or can optionally be combined with the subject matter of one or any combination of Examples 1-17 to include such subject matter, comprising a sensing circuit configured to generate a sensed cardiac signal representative of cardiac activity of a subject; an arrhythmia detection circuit configured to detect an episode of atrial fibrillation (AF) in the sensed cardiac signal using a AF detection criterion; a memory; and a control circuit. The control circuit is configured to: initiate sensing of the cardiac signal during a specified detection time duration as an AF detection window; initiate sensing of the cardiac signal during a first AF detection window and a second consecutive AF detection window; and trigger storage of sampled values of the sensed cardiac signal in response to detecting AF during both the first and second detection windows.

In Example 19, the subject matter of Example 18 optionally includes an arrhythmia detection circuit is configured to: monitor information corresponding to ventricular depolarization (V-V) intervals; determine a V-V interval distribution using sampled V-V interval values; determine a heart rate density index (HRDI) as a portion of the sampled V-V interval values corresponding to a V-V interval occurring most often in the distribution; compare the HRDI to a specified HRDI threshold value; and generate an indication of AF when the determined HRDI satisfies the HRDI threshold value.

In Example 20, the subject matter of one or both of Examples 18 and 19 optionally includes an arrhythmia detection circuit is configured to: determine differences between the V-V intervals; determine a measure of V-V interval dispersion using the determined V-V interval differences; compare the measure of V-V interval dispersion to a specified dispersion threshold value; and generate an indication of AF when the determined measure of V-V dispersion satisfies the specified dispersion threshold value.

Example 21 can include, or can optionally be combined with any portion or combination of any portions of any one or more of Examples 1-20 to include, subject matter that can include means for performing any one or more of the functions of Examples 1-20, or a machine-readable medium including instructions that, when performed by a machine, cause the machine to perform any one or more of the functions of Examples 1-20.

These non-limiting examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like. In some examples, a carrier medium can carry code implementing the methods. The term "carrier medium" can be used to represent carrier waves on which code is transmitted.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
 a sensing circuit configured to generate sampled values of a sensed cardiac signal representative of cardiac activity of a subject;
 an arrhythmia detection circuit electrically coupled to the sensing circuit and configured to apply atrial fibrillation (AF) detection criteria to the sensed cardiac signal, the AF detection criteria including:
 a primary AF detection criterion configured to detect an episode of AF in the sensed cardiac signal; and
 a secondary AF detection criterion configured to confirm the detection of the episode of AF in response to detection by the primary AF detection criterion, wherein the primary AF detection criterion has greater sensitivity to AF detection than the secondary AF detection criterion, and the secondary AF detection criterion has greater specificity to AF detection than the primary AF detection criterion;
 a memory; and
 a control circuit configured to store the sampled values of the sensed cardiac signal that includes the episode of AF in the memory when the episode of AF is detected by the primary AF detection criterion and detection of the episode of AF is confirmed by the secondary AF detection criterion.

2. The apparatus of claim 1, wherein the arrhythmia detection circuit is configured to:
 monitor sampled ventricular depolarization (V-V) interval values of the subject using the sampled values of the sensed cardiac signal;
 determine a V-V interval distribution using the sampled V-V interval values; and
 wherein the arrhythmia detection circuit, according to the second AF detection criterion, is further configured to:
 determine a heart rate density index (HRDI) as a portion of the sampled V-V interval values corresponding to a V-V interval occurring most often in the distribution;
 compare the HRDI to a specified HRDI threshold value included in the secondary AF detection criterion; and
 generate an indication of the AF when the determined HRDI is less than or equal to the HRDI threshold value.

3. The apparatus of claim 2, wherein the arrhythmia detection circuit, according to the primary AF detection criterion, is configured to:
 determine a heart rate mode as the heart rate corresponding to a V-V interval value having most samples in the V-V interval distribution;
 compare the heart rate mode to a specified heart rate mode threshold value included in the first AF detection criterion; and
 generate the indication of AF when the heart rate mode satisfies the specified heart rate mode threshold value.

4. The apparatus of claim 2, wherein the arrhythmia detection circuit, according to the primary AF detection criterion, is configured to:
 determine differences between the V-V intervals;
 determine a measure of V-V interval dispersion using the determined V-V interval differences;
 compare the measure of V-V interval dispersion to a specified dispersion threshold value included in the first AF detection criterion; and
 generate the indication of AF when the determined measure of V-V dispersion satisfies the specified dispersion threshold value.

5. The apparatus of claim 1, including a physiological sensor circuit configured to generate a physiological signal that includes physiological information of the subject, wherein the arrhythmia detection circuit is configured to apply the secondary AF detection criterion to the sensed physiological signal to confirm the detection of the episode of AF.

6. The apparatus of claim 5, wherein the physiological sensor circuit includes at least one of a heart sound sensor circuit and a pulmonary arterial pressure sensor circuit.

7. The apparatus of claim 1, wherein the memory includes a template signal representative of AF, wherein the arrhythmia detection circuit includes a scoring module configured to determine a score associated with correlation of morphology of the sensed cardiac signal to morphology of the template signal representative of AF, and wherein at least one of the primary AF detection criterion and the secondary AF detection criterion is configured to detect an episode of AF when the determined score indicates correlation to the template signal.

8. The apparatus of claim 1, wherein the memory that includes a first onset buffer and a second event storage buffer, and wherein the control circuit is configured to: store the sampled values of the sensed cardiac signal in the onset buffer and overwrite sampled values previously stored in the onset buffer; and initiate, in response to the AF detection by the primary criteria and the confirmation of the detection of the AF episode by the secondary AF detection criteria, storing of the sampled values stored in the onset buffer in the event storage buffer and storing subsequently sampled values of the sensed cardiac signal in the event storage buffer.

9. The apparatus of claim 1, wherein the control circuit is configured to store the sampled values of the cardiac signal in the memory in response to detecting the episode of AF using the primary AF detection criterion, wherein the arrhythmia detection circuit is configured to confirm the detection of the episode of AF using the secondary AF detection criterion using the stored sampled values of the cardiac signal and generate an indication of the detection of AF, and wherein the control circuit is further configured to continue the storing of the sampled values of the cardiac signal in response to the generated indication of AF.

10. The apparatus of claim 1,
wherein the control circuit is configured to store the sampled values for a first segment of the cardiac signal in the memory for a first time duration in response to the arrhythmia detection circuit detecting the episode of AF using the primary AF detection criterion,
wherein the arrhythmia detection circuit is configured to apply the secondary AF detection criterion to the stored values of the first cardiac signal segment,
wherein the control circuit is configured to store sampled values for one or more cardiac signal segments having a second time duration less than the first duration when AF is detected by the primary AF detection criterion and detection of AF is confirmed by the secondary AF detection criterion,
wherein the arrhythmia circuit is configured to apply the secondary AF detection criterion to the one or more cardiac signal segments having the second time duration, and
wherein the control circuit is configured to continue to store sampled values for cardiac signal segments of the second time duration when the arrhythmia detection circuit continues to detect AF in the one or more cardiac signal segments having the second time duration.

11. The apparatus of claim 1, wherein the control circuit is configured to determine that no sampled values of the segment of the cardiac signal have been stored for a specified period of time and, in response to the determination, store the memory of sampled values of a segment of the cardiac signal that includes the episode of AF when the episode of AF is detected only by the primary AF detection criterion.

12. The apparatus of claim 1, including a therapy circuit configured for coupling to electrodes to provide an anti-arrhythmic cardiac therapy to a subject, wherein the arrhythmia detection circuit is configured to generate an indication of confirmation of the episode of AF, and wherein the control circuit is configured to initiate delivery of an anti-arrhythmic therapy in response to the generated indication of confirmation of AF.

13. The apparatus of claim 1, wherein the sensing circuit is configured to be coupled to at least one of an implantable electrode configured for placement in a heart chamber or a subcutaneously implantable electrode that is configured to sense cardiac signals without direct cardiac contact with the subject.

14. The apparatus of claim 1, wherein the apparatus is handheld or wearable.

15. The apparatus of claim 1, wherein the primary AF detection criterion utilizes a V-V interval dispersion criteria and the secondary AF detection criterion utilizes a second criteria different than the V-V interval dispersion criteria.

16. The apparatus of claim 1, wherein the arrhythmia detection circuit is configured to time a primary detection window and a confirmation detection window, and apply the primary AF detection criterion during the primary AF detection window and apply the secondary AF detection criterion to the confirmation detection window triggered by AF detection using the primary AF detection criterion.

17. A system comprising:
a first device including a sensing circuit configured to generate sampled values of a sensed cardiac signal representative of cardiac activity of a subject; and
a second device including:
an arrhythmia detection circuit electrically coupled to the sensing circuit and configured to apply atrial fibrillation (AF) detection criteria to the sensed cardiac signal, the AF detection criteria including:
a primary AF detection criterion configured to detect an episode of AF in the sensed cardiac signal; and
a secondary AF detection criterion configured to confirm the detection of the episode of AF in response to detection by the primary AF detection criterion, wherein the primary AF detection criterion has greater sensitivity to AF detection than the secondary AF detection criterion, and the secondary AF detection criterion has greater specificity to AF detection than the primary AF detection criterion;
a memory; and
a control circuit configured to store the sampled values of the cardiac signal that includes the episode of AF in the memory when the episode of AF is detected by the primary AF detection criterion and detection of the episode of AF is confirmed by the secondary AF detection criterion.

18. The system of claim 17, wherein the arrhythmia detection circuit of the second device is configured to:
monitor sampled ventricular depolarization (V-V) interval values of the subject using the sampled values of the sensed cardiac signal;
determine a V-V interval distribution using the sampled V-V interval values; and
wherein the arrhythmia detection circuit, according to the secondary AF detection criterion, is further configured to:
determine a heart rate density index (HRDI) as a portion of the sampled V-V interval values corresponding to a V-V interval occurring most often in the distribution;
compare the HRDI to a specified HRDI threshold value included in the secondary AF detection criterion; and
generate an indication of the AF when the determined HRDI is less than or equal to the HRDI threshold value.

19. The system of claim 18, wherein the arrhythmia detection circuit of the second device, according to the primary AF detection criterion, is configured to:
determine differences between the V-V intervals;
determine a measure of V-V interval dispersion using the determined V-V interval differences;
compare the measure of V-V interval dispersion to a specified dispersion threshold value included in the primary AF detection criterion; and
generate the indication of AF when the determined measure of V-V dispersion satisfies the specified dispersion threshold value.

20. The system of claim 17, wherein the primary AF detection criterion utilizes V-V interval dispersion criteria to detect AF, and the secondary AF detection criterion utilizes a second criteria different than the V-V interval dispersion criteria to detect AF.

* * * * *